US010499977B2

(12) United States Patent
Van Tol et al.

(10) Patent No.: US 10,499,977 B2
(45) Date of Patent: Dec. 10, 2019

(54) SURGICAL INSTRUMENTS AND METHODS FOR PERFORMING TONSILLECTOMY AND ADENOIDECTOMY PROCEDURES

(71) Applicant: COVIDIEN LP, Mansfield, MA (US)

(72) Inventors: David J. Van Tol, Boulder, CO (US); Gary M. Couture, Ward, CO (US); Robert M. Sharp, Boulder, CO (US); John R. Twomey, Superior, CO (US); Barry J. Kaup, Broomfield, CO (US)

(73) Assignee: Covidien LP, Mansfield, MA (US)

( * ) Notice: Subject to any disclaimer, the term of this patent is extended or adjusted under 35 U.S.C. 154(b) by 281 days.

(21) Appl. No.: 14/793,859

(22) Filed: Jul. 8, 2015

(65) Prior Publication Data

US 2016/0038222 A1 Feb. 11, 2016

Related U.S. Application Data

(60) Provisional application No. 62/035,792, filed on Aug. 11, 2014, provisional application No. 62/035,775, filed on Aug. 11, 2014.

(51) Int. Cl.

| A61B 18/12 | (2006.01) |
|---|---|
| A61B 18/14 | (2006.01) |
| A61B 18/18 | (2006.01) |
| A61B 90/00 | (2016.01) |

(52) U.S. Cl.
CPC ...... *A61B 18/1445* (2013.01); *A61B 18/1442* (2013.01); *A61B 18/18* (2013.01); *A61B 90/04* (2016.02); *A61B 2018/1455* (2013.01); *A61B 2090/0427* (2016.02); *A61B 2090/0481* (2016.02)

(58) Field of Classification Search
CPC .............. A61B 17/295; A61B 18/1445; A61B 2017/292; A61B 2017/2925; A61B 2090/0427; A61B 2017/2946; A61B 2018/1455

See application file for complete search history.

(56) References Cited

U.S. PATENT DOCUMENTS

| 5,403,312 A | 4/1995 | Yates et al. |
|---|---|---|
| 5,558,671 A | 9/1996 | Yates |
| 5,613,499 A | 3/1997 | Palmer et al. |

(Continued)

*Primary Examiner* — Jaymi E Della
*Assistant Examiner* — Sean W Collins
(74) *Attorney, Agent, or Firm* — Carter, DeLuca & Farrell LLP

(57) ABSTRACT

A method of surgery utilizing an end effector assembly having first and second jaw members defining a grasping area therebetween and a tissue-treating area therebetween. Each of the first and second jaw members defines a knife channel positioned within the grasping area and outside of the tissue-treating area. The end effector assembly is positioned such that the knife channels are positioned adjacent tissue to be removed. Thereafter, the first and/or second jaw members are moved from a spaced-apart position to an approximated position to grasp tissue therebetween, the jaw members are energized for conducting energy through tissue disposed within the tissue-treating area to treat tissue disposed within the tissue-treating area, and a knife is advanced through the knife channels to cut tissue adjacent the tissue-treating area thereby separating tissue.

12 Claims, 4 Drawing Sheets

(56) References Cited

U.S. PATENT DOCUMENTS

| | | | |
|---|---|---|---|
| 5,665,100 A * | 9/1997 | Yoon | A61B 10/06 606/139 |
| 5,688,270 A | 11/1997 | Yates et al. | |
| 5,700,261 A | 12/1997 | Brinkerhoff | |
| 5,797,958 A * | 8/1998 | Yoon | A61B 17/122 606/139 |
| 6,146,399 A | 11/2000 | Lee | |
| 6,361,534 B1 | 3/2002 | Chen et al. | |
| 7,160,298 B2 | 1/2007 | Lawes et al. | |
| 7,270,660 B2 | 9/2007 | Ryan | |
| 7,686,804 B2 | 3/2010 | Johnson et al. | |
| 7,931,649 B2 | 4/2011 | Couture et al. | |
| 8,246,618 B2 | 8/2012 | Bucciaglia et al. | |
| 8,486,107 B2 | 7/2013 | Hinton | |
| 8,636,687 B1 | 1/2014 | Latterell | |
| 8,647,343 B2 | 2/2014 | Chojin et al. | |
| 2002/0111624 A1 | 8/2002 | Witt et al. | |
| 2003/0171747 A1 * | 9/2003 | Kanehira | A61B 17/3201 606/45 |
| 2006/0217709 A1 * | 9/2006 | Couture | A61B 18/1442 606/51 |
| 2007/0173814 A1 * | 7/2007 | Hixson | A61B 18/1445 606/51 |
| 2008/0172048 A1 * | 7/2008 | Martin | A61B 18/1442 606/10 |
| 2010/0179545 A1 | 7/2010 | Twomey et al. | |
| 2010/0274244 A1 * | 10/2010 | Heard | A61B 18/1442 606/45 |
| 2011/0028964 A1 * | 2/2011 | Edwards | A61B 18/1442 606/33 |
| 2014/0148797 A1 * | 5/2014 | Yasunaga | A61B 18/1445 606/31 |

* cited by examiner

SURGICAL INSTRUMENTS AND METHODS FOR PERFORMING TONSILLECTOMY AND ADENOIDECTOMY PROCEDURES

CROSS-REFERENCE TO RELATED APPLICATIONS

This application claims the benefit of, and priority to, U.S. Provisional Patent Application Nos. 62/035,792 and 62/035,775, both of which were filed on Aug. 11, 2014. This application is related to U.S. patent application Ser. No. 14/793,827, filed on Jul. 8, 2015. The entire contents of each of the above applications are hereby incorporated herein by reference.

BACKGROUND

Technical Field

The present disclosure relates to surgical instruments and methods and, more particularly, to surgical instruments and methods for performing tonsillectomy and/or adenoidectomy procedures.

Background of Related Art

The tonsils and adenoids are part of the lymphatic system and are generally located in the back of the throat. These parts of the lymphatic system are generally used for sampling bacteria and viruses entering the body and activating the immune system when warranted to produce antibodies to fight oncoming infections. More particularly, the tonsils and adenoids break down the bacteria or virus and send pieces of the bacteria or virus to the immune system to produce antibodies for fighting off infections.

Inflammation of the tonsils and adenoids (e.g., tonsillitis) impedes the ability of the tonsils and adenoids to destroy the bacteria resulting in a bacterial infection. In many instances, the bacteria remain even after treatment and serve as a reservoir for repeated infections (e.g., tonsillitis or ear infections).

A tonsillectomy and/or adenoidectomy may be performed when infections persist and antibiotic treatments fail. Persistent infection typically leads to enlarged tonsil tissue which may need to be removed since in many cases the enlarged tissue causes airway obstruction leading to various sleep disorders such as snoring or, in some cases, sleep apnea. Some individuals are also born with larger tonsils that are more prone to cause obstruction. An adenoidectomy may also be required to remove adenoid tissue when ear pain persists, or when nose breathing or function of the Eustachian tube is impaired. Often times, tonsillectomy and adenoidectomy procedures are performed at the same time.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

A method of surgery provided in accordance with the present disclosure includes utilizing an end effector assembly including first and second jaw members, each jaw member having an opposed surface. The opposed surfaces define a grasping area therebetween. The jaw members each further include tissue-treating plates disposed thereon. The tissue-treating plates define a tissue-treating area therebetween. Each of the first and second jaw members defines a knife channel positioned within the grasping area and outside of the tissue-treating area. The method further includes positioning the end effector assembly relative to tissue such that the knife channels are positioned adjacent tissue to be removed; moving the jaw members to an approximated position to grasp tissue therebetween; energizing the first and second plates to different potentials for conducting energy through tissue disposed within the tissue-treating area to treat tissue disposed within the tissue-treating area; and advancing a knife at least partially through the knife channels to cut tissue adjacent the tissue-treating area thereby separating tissue.

In an aspect of the present disclosure, the method further includes removing the separated tissue.

In another aspect of the present disclosure, conducting energy through tissue disposed within the tissue-treating area includes conducting energy in a generally parallel orientation relative to the opposed surfaces of the first and second jaw members. Alternatively, energy may be conducted in a generally perpendicular orientation.

In yet another aspect of the present disclosure, one or both of the jaw members includes a dam positioned outside the tissue-treating area on an opposite side thereof relative to the knife channels. In such aspects, positioning the end effector assembly includes positioning the dam adjacent tissue to remain and, during the conducting of energy between the tissue-treating plates, the dam inhibits energy, e.g., thermal and/or electrical energy, from being conducted outside the tissue-treating area towards tissue to remain.

Another method of surgery provided in accordance with the present disclosure includes positioning an end effector assembly relative to tissue such that tissue is disposed between first and second jaw members of the end effector assembly. The first and second jaw members have opposed surfaces that define a tissue-grasping area therebetween and a tissue-treating area therebetween. The tissue-treating area is disposed within the tissue-grasping area. The method further includes moving at least one of the first and second jaw members relative to the other from a spaced-apart position to an approximated position to grasp tissue within the tissue-grasping area, energizing at least one of the first and second jaw members for conducting energy through tissue disposed within the tissue-treating area to treat tissue disposed within the tissue-treating area, and advancing a knife at least partially through tissue grasped within the tissue-grasping but outside the tissue-treating area to cut tissue adjacent the tissue-treating area thereby separating tissue.

In an aspect of the present disclosure, the method further includes removing the separated tissue.

In another aspect of the present disclosure, conducting energy through tissue disposed within the tissue-treating area includes conducting energy in a generally parallel orientation relative to the opposed surfaces of the first and second jaw members.

In yet another aspect of the present disclosure, conducting energy through tissue disposed within the tissue-treating area includes conducting energy in a generally perpendicular orientation relative to the opposed surfaces of the first and second jaw members.

In still another aspect of the present disclosure, at least one of the jaw members includes a dam positioned outside the tissue-treating area. In such aspects, positioning the end effector assembly includes positioning the dam adjacent tissue to remain such that, during the conduction of energy through tissue disposed within the tissue-treating area, the dam inhibits energy from being conducted outside the tissue-treating area towards tissue to remain.

BRIEF DESCRIPTION OF THE DRAWINGS

Various aspects and features of the present disclosure are described herein with reference to the drawings wherein.

DETAILED DESCRIPTION

Figure 1:
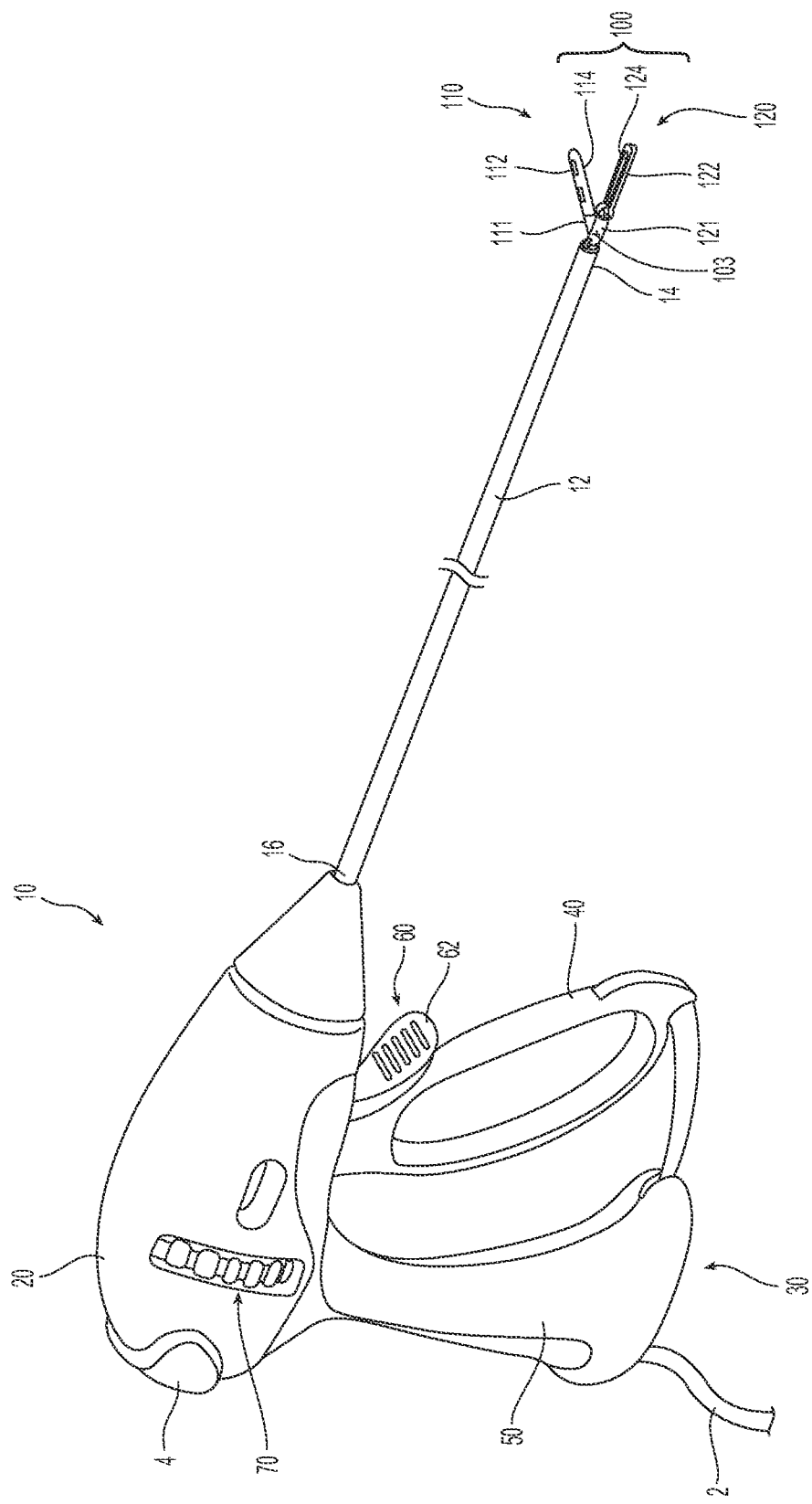
FIG. 1 is a front, side, perspective view of an endoscopic surgical forceps configured for use in accordance with the present disclosure.
Figure 2:
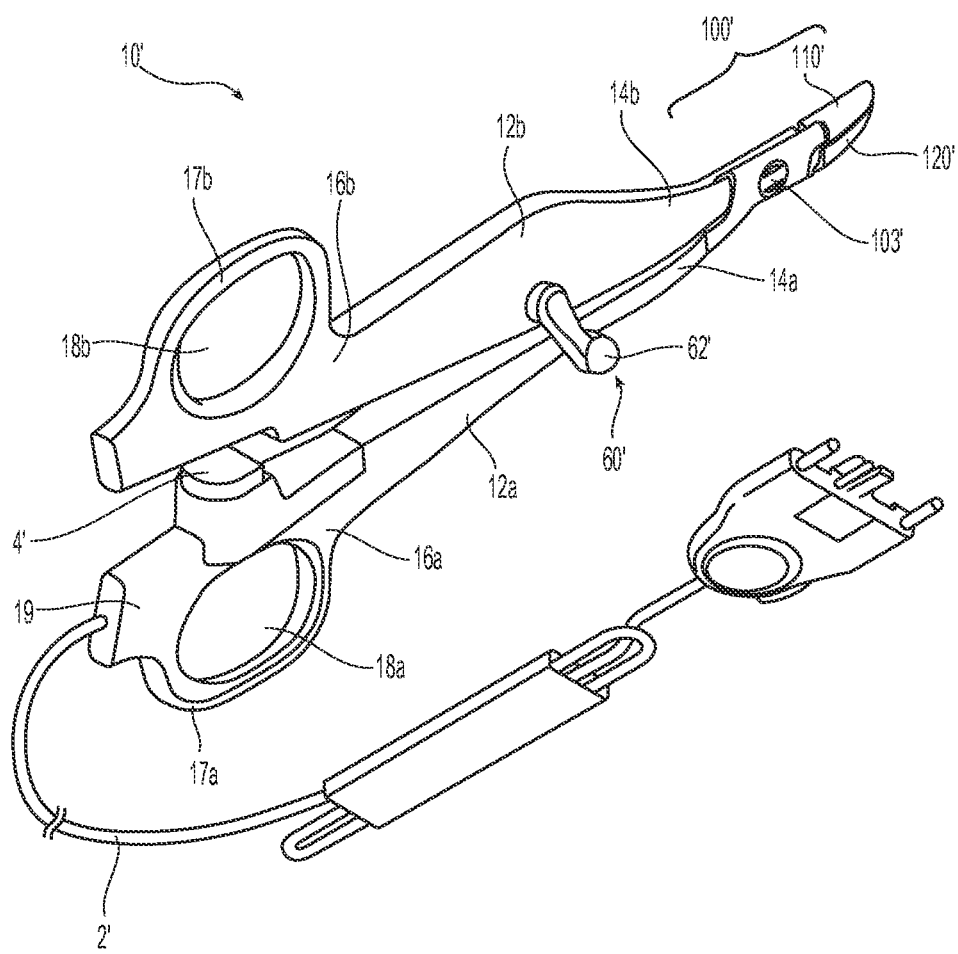
FIG. 2 is a front, side, perspective view of an open surgical forceps configured for use in accordance with the present disclosure.

Turning to FIGS. 1 and 2, FIG. 1 depicts a handheld, shaft-based surgical forceps 10 and FIG. 2 depicts a hemostat-style forceps 10'. For the purposes herein, either forceps 10, forceps 10', or any other suitable surgical instrument may be utilized in accordance with the present disclosure. Obviously, different electrical and mechanical connections and considerations apply to each particular type of instrument; however, the aspects and features of the present disclosure remain generally consistent regardless of the particular instrument used.

Referring to FIG. 1, forceps 10 generally includes a housing 20, a handle assembly 30, a trigger assembly 60, a rotating assembly 70, an activation switch 4, and an end effector assembly 100. Forceps 10 further includes a shaft 12 having a distal end 14 configured to mechanically engage end effector assembly 100 and a proximal end 16 that mechanically engages housing 20. Forceps 10 also includes cable 2 that connects forceps 10 to an energy source (not shown), e.g., a generator or other suitable power source, although forceps 10 may alternatively be configured as a battery-powered device. Cable 2 includes a wire (or wires) (not shown) extending therethrough that has sufficient length to extend through shaft 12 in order to provide energy to one or both tissue-treating plates 114, 124 (FIG. 3B) of jaw members 110, 120, respectively. Activation switch 4 is coupled to tissue-treating plates 114, 124 (FIG. 3B) of jaw members 110, 120, respectively, and the source of energy for selectively activating the supply of energy to jaw members 110, 120 for treating, e.g., cauterizing, coagulating/desiccating, and/or sealing, tissue.

Figure 3A:
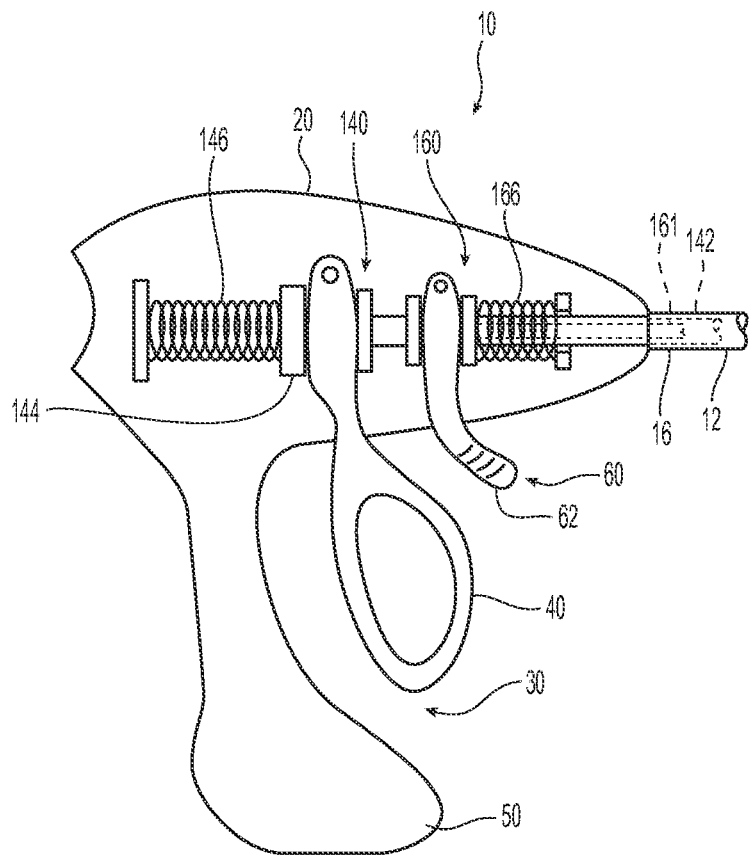
FIG. 3A is a side, cut-away view of the proximal portion of the surgical forceps of FIG. 1, wherein a portion of the housing and some of the internal components thereof have been removed to unobstructively illustrate the handle, knife, and drive assemblies of the forceps.
Figure 3B:
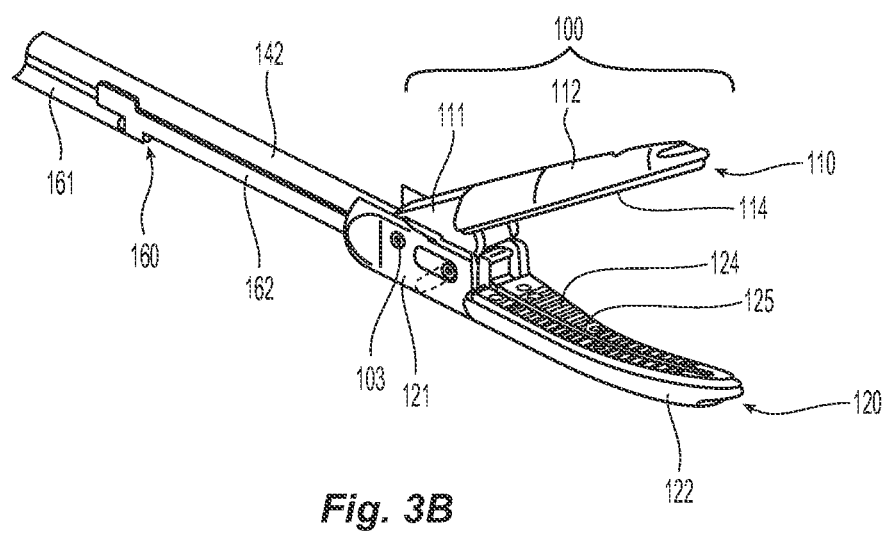
FIG. 3B is a perspective, cut-away view of the distal portion of the surgical forceps of FIG. 1, wherein the shaft has been removed to illustrate the drive bar, knife assembly, and end effector assembly of the forceps.

With additional reference to FIGS. 3A and 3B, handle assembly 30 includes fixed handle 50 and a movable handle 40. Fixed handle 50 is integrally associated with housing 20 and handle 40 is movable relative to fixed handle 50. Movable handle 40 of handle assembly 30 is operably coupled to a drive assembly 140 that, together, mechanically cooperate to impart movement of one or both of jaw members 110, 120 about a pivot 103 between a spaced-apart position and an approximated position to grasp tissue between jaw members 110, 120. In particular, movable handle 40 is coupled to drive bar 142 via a drive mandrel 144 such that movement of movable handle 40 relative to housing 20 effects longitudinal translation of drive bar 142 through housing 20 and shaft 12. The distal end of drive bar 142 is coupled to one or both jaw members 110, 120 such that longitudinal translation of drive bar 142 relative to end effector assembly 100 pivots one or both of jaw members 110, 120 relative to one another. As shown in FIG. 1, movable handle 40 is initially spaced-apart from fixed handle 50 and, correspondingly, jaw members 110, 120 are disposed in the spaced-apart position. Movable handle 40 is depressible from this initial position to a depressed position corresponding to the approximated position of jaw members 110, 120. Further, a biasing member 146 may be disposed within housing 20 and positioned to bias drive bar 142 distally, thereby biasing jaw members 110, 120 towards the spaced-apart position. However, other configurations are also contemplated.

Trigger assembly 60 includes a trigger 62 coupled to housing 20 and movable relative thereto between an un-actuated position and an actuated position for deploying a knife 162 of a knife assembly 160 from a retracted position, wherein knife 162 is positioned proximally of end effector assembly 100, and an extended position, wherein knife 162 extends at least partially between jaw members 110, 120 to cut tissue grasped therebetween. More specifically, trigger 62 is operably coupled to a knife drive bar 161 via a knife drive mandrel 164 such that movement of trigger 62 relative to housing 20 effects longitudinal translation of knife drive bar 161 through housing 20 and shaft 12. The distal end of knife drive bar 161 is coupled to knife 162 such that longitudinal translation of knife drive bar 161 effects translation of knife 162 relative to end effector assembly 100. Trigger 62, as shown in FIG. 1, is initially disposed in the un-actuated position and, correspondingly, knife 162 is disposed in the retracted position. Trigger 62 is selectively actuatable from this un-actuated position to an actuated position corresponding to the extended position of knife 162. Further, a biasing member 166 may be disposed within housing 20 and positioned to bias knife drive bar 161 proximally, thereby biasing knife 162 towards the retracted position and trigger 62 towards the un-actuated position.

Referring to FIG. 2, forceps 10' is shown including two elongated shaft members 12a, 12b, each having a proximal end 16a, 16b, and a distal end 14a, 14b, respectively.

Forceps 10' is configured for use with an end effector assembly 100' similar to end effector assembly 100 (FIGS. 1 and 3B). More specifically, end effector assembly 100' includes first and second jaw members 110', 120' attached to respective distal ends 14a, 14b of shaft members 12a, 12b. Jaw members 110', 120' are pivotably connected about a pivot 103'. Each shaft member 12a, 12b includes a handle 17a, 17b disposed at the proximal end 16a, 16b thereof. Each handle 17a, 17b defines a finger hole 18a, 18b therethrough for receiving a finger of the user. As can be appreciated, finger holes 18a, 18b facilitate movement of the shaft members 12a, 12b relative to one another to, in turn, pivot jaw members 110', 120' from the spaced-apart position, wherein jaw members 110', 120' are disposed in spaced relation relative to one another, to the approximated position, wherein jaw members 110', 120' cooperate to grasp tissue therebetween.

One of the shaft members 12a, 12b of forceps 10', e.g., shaft member 12a, includes a proximal shaft connector 19 configured to connect the forceps 10' to a source of energy (not shown), e.g., a generator. Proximal shaft connector 19 secures a cable 2' to forceps 10' such that the user may selectively supply energy to jaw members 110', 120' for treating tissue, and for energy-based tissue cutting. More specifically, an activation switch 4' is provided for supplying energy to jaw members 110', 120' to treat tissue upon sufficient approximation of shaft members 12a, 12b, e.g., upon activation of activation switch 4' via shaft member 12b.

Forceps 10' further includes a trigger assembly 60' including a trigger 62' coupled to one of the shaft members, e.g., shaft member 12b, and movable relative thereto between an un-actuated position and an actuated position for deploying a knife (not shown, similar to knife 162 of forceps 10' (FIG. 3B)) from a retracted position within one of the shaft members, e.g., shaft member 12b, to an extended position between jaw members 110', 120' for cutting tissue grasped between jaw members 110', 120'.

With reference to FIG. 3B, end effector assembly 100 of forceps 10 (FIG. 1) is shown, although end effector assembly 100 may similarly be used in conjunction with forceps 10' (FIG. 2), or any other suitable surgical instrument. For purposes of simplicity, end effector assembly 100 is described herein as configured for use with forceps 10 (FIG. 1). Further, end effector assembly 100 is generally described below with reference to FIG. 3B, followed by a detailed description, in conjunction with FIGS. 4-8, of various configurations of end effector assemblies suitable for use in performing tonsillectomy and/or adenoidectomy procedures. Each of these configurations may incorporate the general features of end effector assembly 100 and may likewise be used with forceps 10 (FIG. 1), forceps 10' (FIG. 2), or any other suitable surgical instrument. The general features detailed with respect to end effector assembly 100 (FIG. 3B), although applicable to the end effector assemblies of FIGS. 4-8, will not be repeated for purposes of brevity.

Each jaw member 110, 120 of end effector assembly 100 includes a jaw frame having a proximal flange portion 111, 121, an outer insulative jaw housing 112, 122 disposed about the distal portion (not explicitly shown) of each jaw frame, and a tissue-treating plate 114, 124, respectively. Proximal flange portions 111, 121 are pivotably coupled to one another about pivot 103 for moving jaw members 110, 120 between the spaced-apart and approximated positions, although other suitable configurations for allowing the pivoting of jaw members 110, 120 are also contemplated. The distal portions (not explicitly shown) of the jaw frames are configured to support jaw housings 112, 122, and tissue-treating plates 114, 124, respectively, thereon.

Outer insulative jaw housings 112, 122 of jaw members 110, 120 support and retain tissue-treating plates 114, 124 on respective jaw members 110, 120 in opposed relation relative to one another. Tissue-treating plates 114, 124 are formed from an electrically conductive material, e.g., for conducting electrical energy therebetween for treating tissue, although tissue-contacting plates 114, 124 may alternatively be configured to conduct any suitable energy, e.g., thermal, microwave, light, ultrasonic, etc., through tissue grasped therebetween for energy-based tissue treatment. As mentioned above, tissue-treating plates 114, 124 are coupled to activation switch 4 (FIG. 1) and the source of energy (not shown), e.g., via the wires (not shown) extending from cable 2 (FIG. 1) through forceps 10 (FIG. 1), such that energy may be selectively supplied to tissue-treating plate 114 and/or tissue-treating plate 124 and conducted therebetween and through tissue disposed between jaw members 110, 120 to treat tissue.

One or both of jaw members 110, 120 may further include a knife channel 125 (FIG. 3B) defined therein and extending longitudinally therealong. Knife channel(s) 125 (FIG. 3B) are configured to receive a portion of knife 162 (FIG. 3B) as knife 162 (FIG. 3B) is translated from the retracted position to the extended position to guide the translation of knife 162 (FIG. 3B) between jaw members 110, 120.

Various different configurations of end effector assemblies, similar to end effector assembly 100 (FIG. 3B) are detailed below with respect to FIGS. 4-8. Each of these end effector assemblies is configured to facilitate performing tonsillectomy and/or adenoidectomy procedures, although such end effector assemblies may similarly be beneficial for use in a variety of other procedures. To the extent consistent, any of the features of any of these end effector assemblies may be used in conjunction with any or all of the other end effector assemblies described herein.

Figure 4:
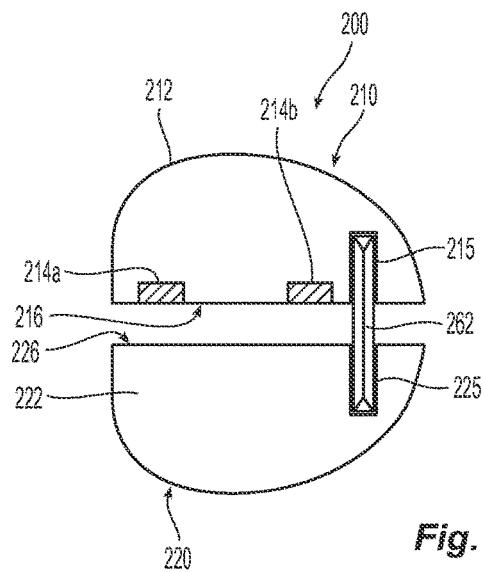
FIG. 4 is a transverse, cross-sectional view of the distal portion of an end effector assembly provided in accordance with the present disclosure and configured for use with the surgical forceps of FIGS. 1 and 2, or any other suitable surgical instrument.

Turning to FIG. 4, end effector assembly 200 includes first and second jaw members 210, 220, respectively. One of the jaw members, e.g., jaw member 210 includes an insulative jaw housing 212 having a pair of spaced-apart, electrically-conductive tissue-treating plates 214a, 214b recessed or partially-recessed within jaw housing 212 to define a planar tissue-grasping surface 216. Tissue-treating plates 214a, 214b are adapted to connect to a source of energy. More specifically, end effector assembly 200 may define a bipolar configuration, wherein plate 214a is charged to a first electrical potential and plate 214b is charged to a second, different electrical potential such that an electrical potential gradient is created for conducting energy between plates 214a, 214b and through tissue grasped between jaw members 210, 220 for treating, e.g., sealing, tissue. In this configuration, energy is conducted between tissue-treating plates 214a, 214b transversely, that is, in a generally parallel direction relative to the plane defined by tissue-grasping surface 216. Further, in this configuration, the tissue-treatment area is defined between tissue-treating plates 214a, 214b. In other words, energy conduction through tissue is substantially confined to the tissue disposed within the peripheral bounds of tissue-treating plates 214a, 214b and, thus only such tissue is treated.

A longitudinally-extending knife channel 215 is defined within tissue-grasping surface 216 of jaw member 210 at a position offset relative to the tissue-treatment area. That is, although knife channel 215 is defined within tissue-grasping surface 216, knife channel 215 is outside the outer bounds of tissue-treating plates 214a, 214b. Such a configuration is advantageous for use in procedures such as tonsillectomy procedures, or other procedures involving the removal of tissue, as bleeding of the tissue to be removed, e.g., tonsil tissue, is not of concern. In fact, treating tissue that is ultimately to be removed is unnecessary. Thus, with respect to end effector assembly 200, the advantage of offset knife travel outside the tissue-treatment area is provided, as is the advantage of providing a knife channel disposed within the tissue-grasping area, which facilitates controlled knife advancement and effective tissue cutting.

Continuing with reference to FIG. 4, the other jaw member, e.g., jaw member 220, defines an insulative jaw housing 222 and an insulative tissue-grasping surface 226. As can be appreciated, upon movement of jaw members 210, 220 to the approximated position, tissue is grasped between tissue-grasping surfaces 216, 226 of jaw members 210, 220, respectively. Jaw member 220 further includes a longitudinally-extending knife channel 225 defined within tissue-grasping surface 226 that is positioned to oppose knife channel 215 of jaw member 210 when jaw members 210, 220 are disposed in the approximated position. Thus, in the approximated position, knife channels 215, 225 cooperate to define a knife guide through which the knife, e.g., knife 262, is translated through upon movement to the extended position.

In use, end effector assembly 200, with jaw members 210, 220 disposed in the spaced-apart position, is manipulated into position such that tissue to be treated and cut is disposed between jaw members 210, 220. With respect to tonsillectomy procedures, for example, end effector assembly 200 is positioned between the cavity wall tissue (or other tissue to remain) and the tonsil tissue (or other tissue to be removed) with knife channels 215, 225 disposed adjacent the tonsil tissue. Once the desired position has been achieved, jaw members 210, 220 are moved to the approximated position to grasp tissue between tissue-grasping surfaces 216, 226. Thereafter, tissue-treating plates 214*a*, 214*b* may be energized to different electrical potentials for conducting energy between plates 214*a*, 214*b* and through tissue grasped between jaw members 210, 220 within the tissue-treatment area to treat such tissue.

Once tissue has been treated the tissue to be removed, e.g., the tonsil tissue, is separated from the tissue to remain, e.g., the wall tissue. In order to separate the tissue, while maintaining jaw members 210, 220 in the approximated position grasping the previously treated tissue therebetween, knife 262 is advanced through knife channels 215, 225 to cut tissue grasped between tissue-grasping surfaces 216, 226 adjacent (but outside the bounds of) the treated tissue. As a result of this configuration, the wall tissue is treated, while knife 262 separates the tonsil tissue to be removed from the wall tissue adjacent the treated wall tissue. The separated tonsil tissue may then be removed using end effector assembly 200, another grasping instrument, a suction device, or via other suitable method.

Figure 5:
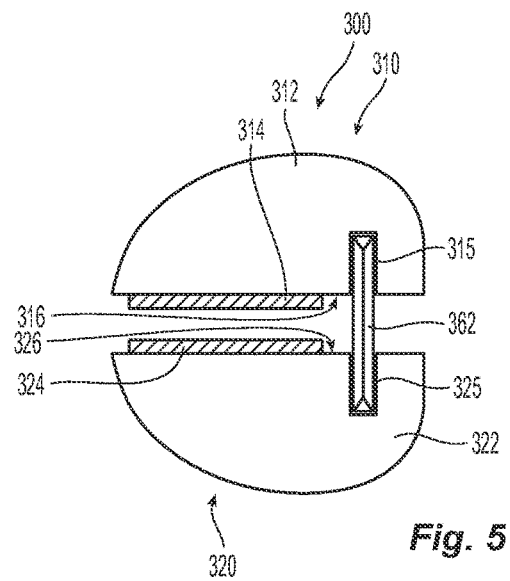
FIG. 5 is a transverse, cross-sectional view of another end effector assembly provided in accordance with the present disclosure and configured for use with the surgical forceps of FIGS. 1 and 2, or any other suitable surgical instrument.

Turning to FIG. 5, end effector assembly 300 is similar to end effector assembly 200 (FIG. 4). Accordingly, for purposes of brevity, only the differences therebetween will be described in detail below while similarities will be summarily described or omitted entirely.

End effector assembly 300 includes first and second jaw members 310, 320, respectively, each including a respective insulative jaw housing 312, 322 defining a tissue-grasping surface 316, 326, respectively. Each jaw member 310, 320 further includes an electrically-conductive tissue-treating plate 314, 324 recessed or partially-recessed within the respective tissue-grasping surfaces 316, 326 such that tissue-grasping surfaces 316, 326 define generally planar configurations. Plates 314, 324 are adapted to connect to a source of energy. End effector assembly 300 may define a bipolar configuration, wherein plate 314 is charged to a first electrical potential and plate 324 is charged to a second, different electrical potential such that an electrical potential gradient is created for conducting energy between plates 314, 324 and through tissue grasped between tissue-grasping surfaces 316, 326 in the tissue-treatment area for treating tissue. In this configuration, in contrast to end effector assembly 200 (FIG. 4), energy is conducted through tissue grasped between plates 314, 324 in a generally perpendicular direction relative to the planes defined by opposed surfaces 316, 326. However, similar to end effector assembly 200 (FIG. 4), the tissue-treatment area is defined between tissue-treating plates 314, 324. Thus, energy conduction through tissue is substantially confined to tissue disposed within the peripheral bounds of tissue-treating plates 314, 324 and, accordingly, only such tissue is treated.

Similarly as detailed above with respect to end effector assembly 300 (FIG. 4), a longitudinally-extending knife channel 315, 325 is defined within the tissue-grasping surface 316, 326 of jaw members 310, 320. Knife channels 315, 325 are disposed in alignment with one another and are positioned outside the outer bounds of the tissue-treatment area defined between plates 314, 324. In the approximated position of jaw members 310, 320, knife channels 315, 325 cooperate to define a knife guide through which the knife, e.g., knife 362, is translated through upon movement to the extended position. End effector assembly 300 may include any of the additional features and advantages noted above with respect to end effector assembly 200 (FIG. 4). Likewise, the use of end effector assembly 300 is similar to that of end effector assembly 200 (FIG. 4).

Figure 6:
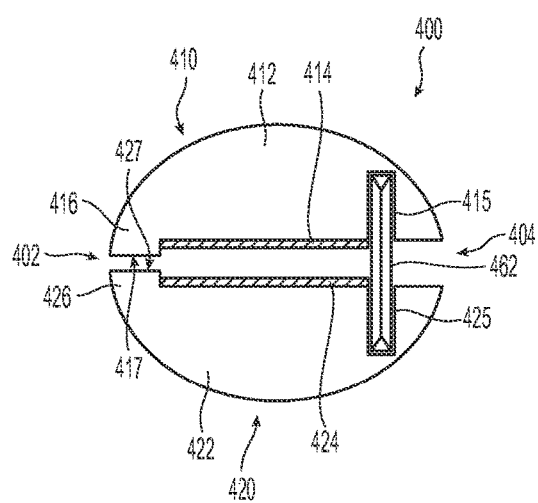
FIG. 6 is a transverse, cross-sectional view of still another end effector assembly provided in accordance with the present disclosure and configured for use with the surgical forceps of FIGS. 1 and 2, or any other suitable surgical instrument.

Turning now to FIG. 6, end effector assembly 400 includes first and second jaw members 410, 420, respectively, each including a respective insulative jaw housing 412, 422 and an electrically-conductive tissue-treating plate 414, 424 disposed on the opposed surface of the respective jaw housing 412, 422. Plates 414, 424 are adapted to connect to a source of energy. End effector assembly 400 may define a bipolar configuration, wherein plate 414 is charged to a first electrical potential and plate 424 is charged to a second, different electrical potential such that an electrical potential gradient is created for conducting energy between plates 414, 424 and through tissue grasped therebetween for treating tissue. Similarly as above, the tissue-treatment area is defined between tissue-treating plates 414, 424. Thus, energy conduction through tissue is substantially confined to tissue disposed within the peripheral bounds of tissue-treating plates 414, 424 and, accordingly, only such tissue is treated.

In order to inhibit energy, e.g., electrical and/or thermal energy, from being conducted outside the tissue-treatment area defined between tissue-treating plates 414, 424 adjacent a first side 402 of end effector assembly 400, each jaw member 410, 420 includes an insulative dam 416, 426 defining a raised surface 417, 427, respectively. Raised surfaces 417, 427 of dams 416, 426 are disposed outside the outer boundaries of the tissue-treatment area and are configured to abut one another in the approximated position of jaw members 410, 420. Being insulative, dams 416, 426 inhibit the conduction of energy outside of the tissue-treatment area on first side 402 of end effector assembly 400. Dams 416, 426 may further be configured to set a minimum gap distance between jaw members 410, 420 in the approximated position. More specifically, dams 416, 426 may cooperate to define a total height, e.g., the sum of their respective heights relative to the opposed surfaces of pates 414, 424, of between about 0.001 inches and about 0.010 inches to achieve a similar minimum gap distance between jaw members 410, 420 in the approximated position.

Continuing with reference to FIG. 6, a longitudinally-extending knife channel 415, 425 is defined within the jaw body 412, 422 of respective jaw members 410, 420 at a position offset relative to the tissue-treatment area on second side 404 of end effector assembly 400, e.g., on the opposite side as compared to dams 416, 426. That is, although knife channels 415, 425 are still disposed within the tissue-grasping area defined between jaw members 410, 420, knife channels 415, 425 are disposed outside the outer bounds of tissue-treating plates 414, 424, e.g., outside the tissue-treatment area. Such a configuration provides similar advantages as detailed above.

In use, end effector assembly 400, with jaw members 410, 420 disposed in the spaced-apart position, is manipulated into position such that tissue to be treated and cut is disposed between jaw members 410, 420. With respect to tonsillectomy procedures, for example, end effector assembly 400 is positioned between the cavity wall tissue (or other tissue to remain) and the tonsil tissue (or other tissue to be removed) such that first side 402 of end effector assembly 400 is positioned adjacent the wall tissue, e.g., such that dams 416, 426 are positioned adjacent the wall tissue, and such second side 404 of end effector assembly 400 is positioned adjacent the tonsil tissue to be removed, e.g., such that knife channels 415, 425 are positioned adjacent the tonsil tissue to be removed. Once the desired position has been achieved, jaw members 410, 420 are moved to the approximated position to grasp tissue therebetween. Thereafter, tissue-treating plates 414, 424 may be energized to different electrical potentials for conducting energy between plates 414, 424 and through tissue grasped between jaw members 410, 420 within the tissue-treatment area to treat such tissue. As noted above, dams 416, 426 help to protect the wall tissue, disposed on first side 402 of end effector assembly 400, from thermal and/or other energy-related damage. Although some heating of tissue adjacent second side 404 of end effector assembly 400 due to energy escaping the tissue-treatment area may occur, such an occurrence is not a concern as the tissue on second side 404 of end effector assembly 400 is ultimately to be removed.

Once tissue has been treated the tissue to be removed, e.g., the tonsil tissue, is separated from the tissue to remain, e.g., the wall tissue. In order to separate the tissue, while maintaining jaw members 410, 420 in the approximated position grasping the previously treated tissue therebetween, knife 462 is advanced through knife channels 415, 425 to cut tissue grasped between jaw members 410, 420 on second side 404 of end effector assembly 400 adjacent (but outside the bounds of) the treated tissue. As a result of this configuration, the wall tissue disposed between jaw members 410, 420 is treated, the wall tissue 410, 420 disposed outside jaw members 410, 420 and adjacent first side 402 of end effector assembly 400 is protected, and the tonsil tissue to be removed, which is disposed on second side 404 of end effector assembly 400, is separated from the wall tissue adjacent the treated wall tissue using knife 462. The separated tonsil tissue may ultimately be removed using end effector assembly 400, another grasping instrument, a suction device, or via other suitable method.

Figure 7:
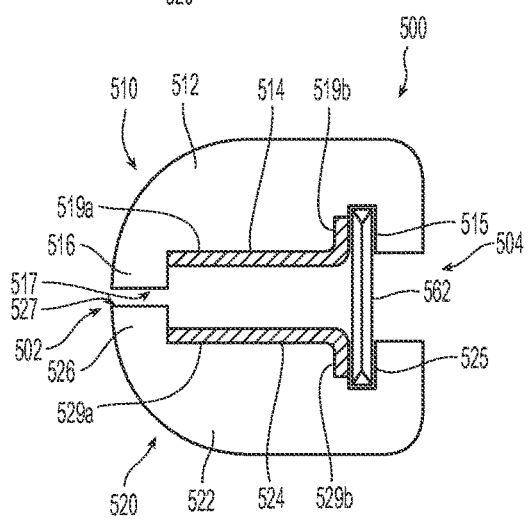
FIG. 7 is a transverse, cross-sectional view of yet another end effector assembly provided in accordance with the present disclosure and configured for use with the surgical forceps of FIGS. 1 and 2, or any other suitable surgical instrument.

Referring to FIG. 7, end effector assembly 500 is similar to end effector assembly 400 (FIG. 6). Accordingly, for purposes of brevity, only the differences therebetween will be described in detail below while similarities will be summarily described or omitted entirely.

End effector assembly 500 includes first and second jaw members 510, 520, respectively, each including a respective insulative jaw housing 512, 522 and an electrically-conductive tissue-treating plate 514, 524 disposed on the opposed surface of the respective jaw housing 512, 522. Plates 514, 524 are adapted to connect to a source of energy and similarly as detailed above with respect to end effector assembly 400 (FIG. 6), may define a bipolar configuration for treating tissue disposed within the tissue-treatment area defined therebetween. Each jaw member 510, 520 further includes a dam 516, 526 defining a raised surface 517, 527, respectively, positioned adjacent first side 502 of end effector assembly 500 outside the tissue-treatment area; and a longitudinally-extending knife channel 515, 525 is defined within the respective jaw body 512, 522 outside the tissue-treatment area on second side 504 of end effector assembly 500 for receipt of a knife 562 therethrough.

End effector assembly 500 differs from end effector assembly 400 (FIG. 6) in that tissue-treating plates 514, 524 of jaw members 510, 520, respectively, of end effector assembly 500, in addition to including a tissue-contacting portion 519a, 529a extending along the respective opposed surfaces thereof, each tissue-treating plate 514, 524 further includes an arm 519b, 529b extending inwardly towards the respective insulative jaw housing 512, 522 in a generally perpendicular direction relative to tissue-contacting portions 519a, 529a, respectively. Arms 519b, 529b are positioned adjacent knife channels 515, 525 and extending in generally parallel relation relative to knife channels 515, 525.

In use, arms 519b, 529b and, more particularly, the generally L-shaped corner defined at the interface between tissue-contacting portions 519a, 529a and arms 519b, 529b, respectively, create a region of increased current concentration adjacent knife channels 515, 525 when energy is conducted between plates 514, 524 to treat tissue disposed within the tissue-treatment area defined between tissue-contacting portions 519a, 529a of plates 514, 524, respectively. This region of increased current concentration facilitates the eventual mechanical cutting of tissue adjacent knife channels 515, 525 using knife 562 and/or effects pre-cutting of such tissue while energy is conducted through tissue disposed within the tissue-treatment area to treat such tissue. The configuration and use of end effector assembly 500 may otherwise be similar to that of end effector assembly 400 (FIG. 6), detailed above.

Figure 8:
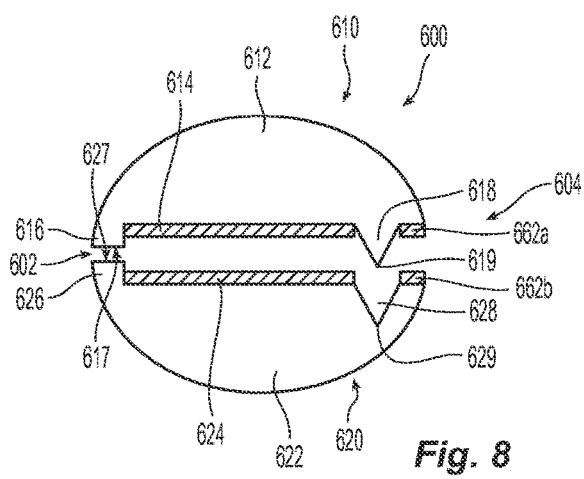
FIG. 8 is a transverse, cross-sectional view of still yet another end effector assembly provided in accordance with the present disclosure and configured for use with the surgical forceps of FIGS. 1 and 2, or any other suitable surgical instrument.

Turning to FIG. 8, end effector assembly 600 is similar to end effector assembly 400 (FIG. 6). Accordingly, for purposes of brevity, only the differences therebetween will be described in detail below while similarities will be summarily described or omitted entirely.

End effector assembly 600 includes first and second jaw members 610, 620, respectively, each including a respective insulative jaw housing 612, 622 and an electrically-conductive tissue-treating plate 614, 624 disposed on the opposed surface of the respective jaw housing 612, 622. Plates 614, 624 are adapted to connect to a source of energy and, similarly as detailed above with respect to end effector assembly 400 (FIG. 6), may define a bipolar configuration for treating tissue disposed within the tissue-treatment area defined therebetween. Each jaw member 610, 620 further includes a dam 616, 626 defining a raised surface 617, 627, respectively, positioned adjacent first side 602 of end effector assembly 600 outside the tissue-treatment area.

End effector assembly 600 differs from end effector assembly 400 (FIG. 6) in that, rather than providing knife channels for reciprocation of a knife therethrough, end effector assembly 600 defines a static cutting configuration. More specifically, one of the jaw members, e.g., jaw member 610, an insulative cutting member 618 extending from jaw body 612 towards jaw member 620 on the second side 604 of end effector assembly 600, e.g., on the opposite side of plates 614, 624 as dams 616, 626. Cutting member 618 extends longitudinally along jaw member 610 and defines a generally triangular transverse, cross-sectional configuration having an apex edge 619 which may be sharp, although other configurations are also contemplated.

The other jaw member, e.g., jaw member 620, includes an insulative recess 628 defined within jaw housing 622 thereof and positioned to oppose cutting member 618. Recess 628 extends longitudinally along jaw member 620 and defines a generally triangular transverse, cross-sectional configuration that is complementary to the configuration of cutting member 618 so as to at least partially receive cutting member 618 therein upon approximation of jaw members 610, 620. Valley edge 629 of recess 628 is defined at the valley of recess 628.

End effector assembly 600 further differs from end effector assembly 400 (FIG. 6) in that jaw members 610, 620 each further include an electrically-conductive cutting plate 662a, 662b disposed thereon adjacent second side 604 of end effector assembly 600 such that cutting member 618 and recess 628 are disposed between tissue-treating plates 614, 624 and respective cutting plates 662a, 662b. Cutting plates 662a, 662b are adapted to connect to a source of energy and, in use, are configured to be energized to the same potential as the corresponding tissue-treating plate 614, 624 of the respective jaw member 610, 620. Cutting plates 662a, 662b define reduced widths as compared to tissue-treating plates 614, 624. Sufficient width for tissue treatment is not required, as cutting plates 662a, 662b are not concerned with treating tissue disposed therebetween (although some treatment of the tissue disposed therebetween may occur). Rather, cutting plates 662a, 662b are provided to facilitate creation of an increased current concentration region between cutting member 618 and recess 628 such that, as detailed below, the increased current concentration, in combination with the high pressure concentration between apex edge 619 and valley edge 629 of cutting member 618 and recess 628, respectively, electromechanically cuts tissue disposed therebetween.

In use, with respect to tonsillectomy procedures, for example, end effector assembly 600 is positioned between the cavity wall tissue (or other tissue to remain) and the tonsil tissue (or other tissue to be removed) such that first side 602 thereof is disposed adjacent the wall tissue and such that cutting member 618 and recess 628 are disposed adjacent the tonsil tissue. Once the desired position has been achieved, jaw members 610, 620 are moved to the approximated position to grasp tissue therebetween and tissue-treating plates 614, 624 are energized to different electrical potentials for conducting energy therebetween and through tissue grasped within the tissue-treatment area defined between plates 614, 624 to treat such tissue.

In addition to tissue-treating plates 614, 624 being energized, cutting plates 662a, 662b are likewise energized such that, concomitantly with the treatment of tissue disposed within the tissue-treatment area, tissue disposed between cutting member 618 and recess 628, due to the increased current and pressure concentrations therebetween, is cut, thereby separating the tonsil tissue to be removed from the treated wall tissue. The separated tonsil tissue may then be removed using end effector assembly 600, another grasping instrument, a suction device, or via other suitable method.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method of surgery, comprising:
positioning an end effector assembly relative to tissue, the end effector assembly including first and second jaw members, each jaw member defining outer lateral sides and having an opposed surface disposed between the outer lateral sides, the opposed surfaces defining a grasping area therebetween, the grasping area defining a length extending between proximal and distal ends of the opposed surfaces and a width extending between first and second sides of the opposed surfaces, the end effector assembly further including a tissue-treating plate disposed on each of the jaw members, the tissue-treating plates defining a tissue-treating area therebetween, the tissue-treating area defining a width less than the width of the grasping area, each of the jaw members defining a knife channel therein, each knife channel extending along at least a portion of the length of the grasping area within the grasping area at a position laterally offset from the outer lateral sides of the first and second jaw members, the knife channel of each of the jaw members separating the tissue-treating area from a non-tissue treating area, the non-tissue treating area extending along the entire knife channel of each of the jaw members, wherein the end effector assembly is positioned relative to the tissue such that the knife channels are disposed between a first portion of the tissue and a second portion of the tissue;
moving at least one of the jaw members relative to the other from a spaced-apart position to an approximated position to grasp the first portion of the tissue within the tissue-treating area and to grasp the second portion of the tissue within the grasping area but outside of the tissue-treating area;
energizing the tissue-treating plates to conduct energy through the first portion of the tissue to treat the first portion of the tissue without treating the second portion of the tissue with the energy; and
advancing a knife at least partially through the knife channels such that the knife is advanced between the jaw members along the at least the portion of the length of the grasping area within the grasping area at the position laterally offset from the outer lateral sides of the jaw members and the tissue-treating area to cut tissue between the first portion of the tissue and the second portion of the tissue, thereby separating the second portion of the tissue from the first portion of the tissue.

2. The method according to claim 1, further including removing the second portion of the tissue.

3. The method according to claim 1, wherein the energy is conducted through the first portion of the tissue in a generally parallel orientation relative to the opposed surfaces of the first and second jaw members.

4. The method according to claim 1, wherein the energy is conducted through the first portion of the tissue in a generally perpendicular orientation relative to the opposed surfaces of the first and second jaw members.

5. The method according to claim 1, wherein at least one of the jaw members includes a dam positioned outside the tissue-treating area on an opposite side thereof relative to the knife channels, wherein positioning the end effector assembly includes positioning the dam between the first portion of the tissue and a third portion of the tissue and wherein, the dam inhibits the energy from being conducted outside the tissue-treating area towards the third portion of the tissue.

6. The method according to claim 1, wherein the knife channel of each of the jaw members separates the tissue-treating plates from the non-tissue treating area.

7. The method according to claim 1, wherein the tissue treating plates each further include an arm extending along a lateral side of the corresponding knife channel of each of the jaw members.

8. A method of surgery, comprising:
positioning an end effector assembly relative to tissue such that the tissue is disposed between first and second jaw members of the end effector assembly, the first and second jaw members having outer lateral sides and opposed surfaces extending between the outer lateral sides, the opposed surfaces defining a tissue-grasping area therebetween having a length and a width and a tissue-treating area therebetween having a width less than the width of the tissue-grasping area, the tissue-treating area disposed within the tissue-grasping area, each of the jaw members defining a knife channel therein, each knife channel extending along at least a portion of the length of the tissue-grasping area at a position laterally offset from the outer lateral sides of the first and second jaw members, the knife channel of each of the jaw members separating the tissue-treating area from a non-tissue treating area, the non-tissue treating area extending along the entire knife channel of each of the jaw members;
moving at least one of the jaw members relative to the other from a spaced-apart position to an approximated position to grasp a first portion of the tissue within the tissue-treating area and to grasp a second portion of the tissue within the tissue-grasping area but laterally offset outside of the tissue-treating area;
energizing at least one of the jaw members for conducting energy through the first portion of the tissue to treat the first portion of the tissue without treating the second portion of the tissue with the energy; and
advancing a knife at least partially between the jaw members along at least a portion of the length of the tissue-grasping area within the tissue-grasping area at the position laterally offset from the outer lateral sides of the jaw members and the tissue-treating area such that the knife is advanced at least partially through the tissue-grasping area but outside the tissue-treating area to cut tissue between the first portion of the tissue and the second portion of the tissue, thereby separating the second portion of the tissue from the first portion of the tissue such that tissue on a first side of the knife includes the treated first portion of tissue and all of the tissue on a second side of the knife opposite the first side of the knife is untreated with the energy.

9. The method according to claim 8, further including removing the second portion of the tissue.

10. The method according to claim 8, wherein conducting the energy through the first portion of the tissue includes conducting the energy in a generally parallel orientation relative to the opposed surfaces of the first and second jaw members.

11. The method according to claim 8, wherein conducting the energy through the first portion of the tissue includes conducting the energy in a generally perpendicular orientation relative to the opposed surfaces of the first and second jaw members.

12. The method according to claim 8, wherein at least one of the jaw members includes a dam positioned outside the tissue-treating area, wherein positioning the end effector assembly includes positioning the dam between the first portion of the tissue and a third portion of the tissue, and wherein, the dam inhibits the energy from being conducted outside the tissue-treating area towards the third portion of the tissue.

\* \* \* \* \*